United States Patent
Reichardt et al.

(10) Patent No.: US 6,395,479 B1
(45) Date of Patent: May 28, 2002

(54) ANDROGEN-METABOLIC GENE MUTATIONS AND PROSTATE CANCER RISK

(75) Inventors: Juergen K. V. Reichardt, Altadena; Gerhard A. Coetzee, La Canada; Brian E. Henderson, San Marino; Nick Makridakis, Glendale; Ronald Ross, Pasadena, all of CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/235,538

(22) Filed: Jan. 22, 1999

Related U.S. Application Data

(60) Provisional application No. 60/072,225, filed on Jan. 23, 1998.

(51) Int. Cl.[7] ............................ C12Q 1/68; C12P 19/34; C07H 21/04
(52) U.S. Cl. ......................... 435/6; 435/91.1; 536/23.1
(58) Field of Search .................... 435/6, 91.1; 536/23.1, 536/24.3

(56) References Cited

U.S. PATENT DOCUMENTS 5,422,262 A  6/1995  Anderson et al.

OTHER PUBLICATIONS

Vogelstein, Trends in Genetics, vol. 9, pp. 138–141, 1993.*
Jaffe et al., Cancer Research, vol. 60, pp. 1626–1630; Mar. 15, 2000.*
Aquilina, J. W., et al., "Androgen Deprivation As A Strategy for Prostate Cancer Chemoprevention" (1997) *J. Natl. Cancer Inst.* 89: 689–696.
Bayer, E.A., et al., "The Avidin–Biotin Complex in Affinity Cytochemistry" (1979) *Meth. Enzym.* 62: 308.
Beaucage, et al., "Deoxynucleoside Phosphoramidites–A New Class of Key Intermediates for Deoxypolynucleotide Synthesis" (1981) *Tet. Lett.* 22: 1859–1862.
Brentano, S. T., et al., "Tissue–Specific, Cyclic Adenosine 3', 5'—Monophosphate–Induced, and Phorbol Ester–Repressed Transcription from the Human P450c17 Promoter in Mouse Cells" (1990) *Mol. Endocrin.* 4:1972–1979.
Carey, A. H., et al., "Polycystic Ovaries and Premature Male Pattern Baldness Are Associated With One Allele of The Steroid Metabolism Gene Cyp17" (1994) *Hum. Mol. Gen.* 3:1873–1876.
Catalona, W. J., et al., "Measurement of Prostate–Specific Antigen in Serum As A Screening Test for Prostate Cancer" (1991) *N. Engl. J. Med.* 324: 1156–61.
Cariello, "Resolution of a Missense Mutant in Human Genomic DNA By Denaturing Gradient Gel Electrophoresis and Direct Sequencing Using In Vitro DNA Amplification: $HPRT_{munich}$" *Human Genetics* 42: 726.
Coffey, D. S., "*The Molecular Biology of the Prostate*", in Prostrate Diseases (1993) pp. 28–56, W.B. Saunders Company.

(List continued on next page.)

Primary Examiner—W. Gary Jones
Assistant Examiner—Jehanne Souaya
(74) Attorney, Agent, or Firm—McCutchen, Doyle, Brown & Enersen, LLP

(57) ABSTRACT

This present invention identifies mutations in several androgen-metabolic genes (SRD5A2, CYP17, HSD3B2, and HSD17B3) and methods of using such mutations in the diagnosis and treatment of inheritable prostate cancer susceptibility. Isolation of genomic DNA of various racial/ethnic populations followed by SSCP scanning and direct PCR sequencing of the aberrant SSCP (single-strand conformation dependent DNA polymorphism) patterns allows for identification of the disclosed polymorphisms. Screening for the disclosed mutations establishes a differential distribution among various racial/ethnic groups as well as altered in vivo enzyme activity that parallels prostate cancer risk.

2 Claims, 5 Drawing Sheets

| Genotype | | African-American Men | | Latino Men | |
|---|---|---|---|---|---|
| Normal | controls | 113 | | 103 | |
| | Stage 1 cases | 50 | | 41 | |
| | Stage 2+ cases | 62 | | 39 | |
| A49T | controls | 1 (1; 0) | | 4 (3; 1) | |
| | Stage 1 cases | 1 (1; 0) | RR=2.3 | 4(3; 1) | RR=2.5 |
| | Stage 2+ cases | 7 (5; 2) | RR=12.8 | 6 (5; 1) | RR=4.0 |
| | | | 1-sided p= 0.0049 | | 1-sided p= 0.039 |

OTHER PUBLICATIONS

Cole, et al., "The EBV–Hybridoma Technique and its Application to Human Lung Cancer" (1985) in *Monoclonal Antibodies and Cancer Therapy*, Alan R. Liss, Inc., pp. 77–96.

Cotton, et al., "Reactivity of Cytosine and Thymine In Single–Base–Pair Mismatches With Hydroxylamine and Osmium Tetroxide and Its Application To The Study OF Mutations" (1988) *Proc. Natl. Acad. Sci. USA* 85: 4397.

Davis, D. L. and Russell, D. W., "Unusual Length Polymorphism in Human Steroid 5α–Reductase Type 2 Gene (SRD5A2)" *Human Molecular Genetics*, (1993) 2: 820.

Devgan, S. A. et al. "Genetic Variation of 3B–Hydroxysteroid Dehydrogenase Type II In Three Racial/Ethnic Groups: *Implications for Prostate Cancer Risk*" The Prostate (1997) 33: 9–12.

Engval, E. et al., "Enzyme–Linked Immunosorbent Assay, ELISA—III. Quantitation of Specific Antibodies by Enzyme–Labeled Anti–Immunoglobulin In Antigen–Coated Tubes" (1972) *The Journal of Immunology* 109: 129.

Finke, R., "Theoretical Basis and Application of Molecular Diagnostics" (1996) *Exp. Clin. Endocrinol. Diabetes* 104 (suppl) : 92–97.

Friedmann, "Gene Therapy" (1991), in Therapy for Genetic Diseases, T. Friedman, ed., *Oxford University Press*, pp. 105–121.

Goding, J.W., "Conjugation of Antibodies With Fluorochromes: Modifications to the Standard Methods" (1976) *J. Immunol. Meth.* 13: 215.

Henderson, B. E. et al., "Endogenous Hormones As A Major Factor in Human Cancer" (1982) *Cancer Res.* 42: 3232–3239.

Hurby, et al. "Application of Synthetic Peptides: Antisense Peptides," in *Synthetic Peptides, A User's Guide*, (1992) W.H. Freeman, NY, pp. 289–307.

Kadohama, N., "Selective Inhibition of Prostatic Tumor 5α–Reductase By A 4–Methyl–4–AZA–Steroid" (1984) *Cancer Res.* 44: 4947–4954.

Kasprzak, et al., "Location Of A Contact Site Between Actin and Myosin in the Three–Dimensional Structure of the Acto–S1 Complex" (1989) *Biochemistry* 28: 9230–8.

Kohler, G. and Milstein, C., "Continuous Cultures of Fused Cells Secreting Antibody of Predefined Specificity" (1975) *Nature* 256: 495–497.

Labrie, F. et al., "Structure of Human Type II 5α–Reductase Gene" (1992) *Endocrinology* 131: 1571–1573.

Labrie, F. et al, "Structure, Function and Tissue–Specific Gene Expression of 3B–Hydroxysteroid Dehydrogenase/5–ENE–4ENE Isomerase Enzymes In Classical and Peripheral Intracrine Steroidogenic Tissues" (1992) *J Steroid Biochem Mol Biol* 43: 805–826.

Lamb, J. C., "Prostatic Involution In Rats Induced By A Novel 5α–Reductase Inhibitor, SK&F 105657: Role For Testosterone In The Androgenic Response" (1992) *Endocrinology* 130: 685–694.

Lookingbill, D.P., "Clinical and Biochemical Parameters of Androgen Action In Normal Healthy Caucasian Versus Chinese Subjects" (1991) *J. Clinical Endocrinology & Metabolism* 72: 1242–1248.

Lutz et al., "The Distribution of Two hnRNP–Associated Proteins Defined By A Monoclonal Antibody Is Altered In Heat–Shocked HeLa Cells" (1988) *Exp. Cell Research* 175: 109–124.

Makridakis, N. et al., "A Prevalent Missense Substitution That Modulates Activity of Prostatic Steroid 5α–Reductase" (1997) *Cancer Res.* 57: 1020–1022.

Mehta, C. R. and Patel, N. R., "A Network Algorithm for Performing Fisher's Exact Test in r×c Contingency Tables" (1983) *J. Am. Stat. Assoc.* 78: 427–434.

Meikle, A. W., "Production, Clearance, and Metabolism of Testosterone In Men With Prostatic Cancer" (1987) *Prostate* 10: 25–31.

Miller, W. L. et al., "The Regulation of 17,20 Lyase Activity" (1997) *Steriods* 62: 133–142.

Montie, J. E. et al., "Staging Systems and Prognostic Factors for Prostate Cancer" (1996) in *Comprehensive Textbook of Genitourinary Oncology*, Vogelzang, NJ et al. (eds.), Williams and Wilkins, Baltimore, MD, pp. 712–722.

Montie, J. E., "*1992 Staging System for Prostate Cancer*" (1993), *Seminars in Urology* 11: 10–13.

Orita, M. et al., "Detection of Polymorphisms of Human DNA by Gel Electrophoresis As Single–Strand Conformation Polymorphisms" (1989) *Proc. Nat. Acad. Sci. USA* 86: 2766–2770.

Osborne, R. J. et al., "Mutations In the P53 Gene In Primary Human Breast Cancers" (1991) *Cancer Res.* 51: 6194–6198.

Parker, S.L. et al., "Cancer Statistics, 1997" (1997) *Cancer J. Clin.* 65: 5–27.

Peltonen, L. and Pulkkinen L., "How to Find A Mutation Behind An Inherited Disease" (1986) *Ann. Clin. Res.* 18: 224–230.

Picado–Leonard, J. and Miller, W. L., "Cloning and Sequence of the Human Gene for P450c17 (Steroid 17α–Hydroxylase/17,20 Lyase): Similarity With the Gene for P450c21" (1987) *DNA* 6: 439–448.

Pollard, M. et al., "The Promotional Effect of Testosterone On Induction of Prostate–Cancer In MNU–Sensitized L–W Rats" (1989) *Cancer Lett.* 45: 209–212.

Reichardt, J. K. V. et al., "Genetic Variability of the Human SRD5A2 Gene: Implications for Prostate Cancer Risk" (1995) *Cancer Res.* 55: 3973–3975.

Reichardt, K. V. et al., "Genetic Variation In the SRD5A2 Gene Encoding Steroid 5α–Reductase Type II and Prostate Cancer Risk" ASHG 46 Annual Meeting, San Francisco. (1996) *Am. J. Hum. Gen.* (suppl) 59: A187.

Rheaume, E. et al, "Congenital Adrenal Hyperplasia Due to Point Mutations in the Type II 3B–Hydroxysteroid Dehydrogenase Gene" (1992) *Nature Genet 1*: 239–245.

Ross, R. K. et al., "5–Alpha–Reductase Activity and Risk of Prostate Cancer Among Japanese and US White and Black Males" (1992) *Lancet* 339: 887.

Ross, R. K. et al., "Does the Racial–Ethnic Variation In Prostate Cancer Risk Have A Hormonal Basis?" (1995) *Cancer* 75: 1778–1782.

Saiki, R. K. et al., "Primer–Directed Enzymatic Amplification of DNA With A Thermostable DNA Polymerase" (1988) *Science* 239: 487–491.

Scharf (1986) "Direct Cloning and Sequence Analysis of Enzymatically Amplified Genomic Sequences" *Science* 233: 1076.

Sheffield, V. C. et al., "Attachment of A 40–Base–Pair G+C–Rich Sequence (GC–Clamp) to Genomic DNA Fragments By the Polymerase Chain Reaction Results in Improved Detection of Single–Base Changes" (1989) *Proc. Nat. Acad. Sci. USA* 86: 232–236.

Shenk et al., "Biochemical Method for Mapping Mutational Alterations In DNA With S1 Nuclease: The Location of Deletions and Temperature–Sensitive Mutations in Simian Virus 40" (1975) *Proc. Natl. Acad. Sci. USA* 72: 989.

Shirai, T. et al., "Site–Specific Effects of Testosterone Propionate On the Prostate of Rat Pretreated With 3,2'–Dimethyl–4–aminobiphenyl: Dose–Dependent Induction of Invasive Carcinomas" (1995) *Jpn. J. Cancer Res.* 86: 645–648.

Silver, R. I. et al., "Expression and Regulation of Steroid 5α–Reductase 2 In Prostate Disease" (1994) *J. Urol.* 152: 433–437.

Smooker, P. M. and Cotton, R. G., "The Use of Chemical Reagents In the Detection of DNA Mutations" (1993) *Mutat. Res.* 288: 65–77.

Sternberger, L. A. et al., "The UnLabeled Antibody Enzyme Method of Immunohistochemistry—Preparation and Properties of Soluble Antigen–Antibody Complex (Horseradish Peroxidase–Antihorseradish Peroxidase) and Its Use In Identification of Spirochetes" (1970) *Histochem. Cytochem.* 18: 315.

Thigpen, A. E. et al., "Molecular Genetics of Steroid 5α–Reductase 2 Deficiency" (1992) *J. Clin. Invest.* 90: 799–809.

Trunnel, J. B. and Duffey, B. J., "The Influence of Certain Steroids On the Behavior of Human Prostatic Cancer" (1950) *Trans. NY Acad. Sci.* 12: 238–241.

Verreault, H. et al, "Dinucleotide Repeat Polymorphisms In the HSD3B2 Gene" (1994) *Hum. Mol. Genet.* 3: 384.

Walsh, P. S. et al. "Preferential PCR Amplification of Alleles: Mechanisms and Solutions" (1992) *PCR Methods Appl.* 1: 241–250.

Wartell, R. M. et al. "Detecting Base Pair Substitutions in DNA Fragments By Temperature–Gradient Gel Electrophores" (1990) *Nucl. Acids Res.* 18: 2699–2705.

Wigley, W. C., et al. "Natural Mutagenesis Study of the Human Steroid 5α–Reductase 2 Isozyme" (1994) *Biochemistry* 33: 1265–1270.

Wilson, J. D. et al. "Steroid 5α–Reductase 2 Deficiency" (1993) *Endocr. Rev.* 14: 577–593.

Wu, A. H., et al., "Serum Androgens and Sex Hormone–Binding Globulins In Relation to Lifestyle Factors in Older African–American, White, and Asian Men in the United States and Canada" (1995) *Cancer Epidemiol. Biomarkers Prev.* 4: 735–741.

Wu, D. Y., et al. "Laboratory Methods: Direct Analysis of Single Nucleotide Variation In Human DNA and RNA Using In Situ Dot Hybridization" (1989) *DNA* 8: 135–142.

Wu, D. Y., et al. "The Ligation Amplification Reaction (LAR)—Amplication of Specific DNA Sequences Using Sequential Rounds of Template–Dependent Ligation" (1989a) *Genomics* 4: 560–569.

Yamaguchi, H., et al. "A 5'–Splice Site Mutation In the Cytochrome P450 Steroid 17α–Hydroxylase Gene in 17α–Hydroxylase Deficiency" (1997) *J. Clin. Endocrin. Metab.* 82: 1934–1938.

* cited by examiner

|  | Racial/Ethnic Group (Subjects) | | | | |
| --- | --- | --- | --- | --- | --- |
| Genotype* | Total (286) | African-American (95) | Caucasian (49) | Latino (40) | Asian (102) |
| VV (%) | 46.5 | 58.9 | 57.1 | 47.5 | 29.4 |
| VL (%) | 42.0 | 37.9 | 38.8 | 37.5 | 49.0 |
| LL (%) | 11.5 | 3.2 | 4.1 | 15.0 | 21.6 |
| Leucine allele (%) | 32.5 | 22.1 | 23.5 | 33.7 | 46.1 |

*VV are valine 39 homozygotes for the V89L substitution, LL are leucine 89 homozygotes, and VL are heterozygotes individuals. The allele frequency of the V89L polymorphism is significantly different in Asians from that in African-Americans ($P = 0.00001$), Caucasians ($P = 0.0002$, and Latinos ($P = 0.041$).

FIG. 3.

| Genotype | AAG (median in ng/ml) (Asian individuals) |
| --- | --- |
| VV | 4.72 (30) |
| VL | 4.05 (50) |
| LL | 3.40 (22) |

* In vivo steroid 5a-reductase activity was measured by assaying serum AAG levels (3, 13). The number of Asian individuals is given in parentheses after each median AAG level. The age-adjusted P for VV versus LL in Asians is 0.04 and 0.02 in all controls studied (data not shown).

FIG. 4.

| Genotype | | African-American Men | | Latino Men | |
|---|---|---|---|---|---|
| Normal | controls | 113 | | 103 | |
| | Stage 1 cases | 50 | | 41 | |
| | Stage 2+ cases | 62 | | 39 | |
| A49T | controls | 1 (1; 0) | | 4 (3; 1) | |
| | Stage 1 cases | 1 (1; 0) | RR=2.3 | 4(3; 1) | RR=2.5 |
| | Stage 2+ cases | 7 (5; 2) | RR=12.8 | 6 (5; 1) | RR=4.0 |
| | | | 1-sided p= 0.0049 | | 1-sided p= 0.039 |

*FIG. 5.*

| Substitution | $K_M$ (T; μM) | $K_M$ (NADPH; μM) | $V_{max}$ (nmol/min/mg) | pH Optimum | Comments |
|---|---|---|---|---|---|
| normal (wild type) | 0.7 (0.3-1.2) | 8 | 1.3 (0.5-1.8) | 6.0 | similar to reported data[9] |
| A49T | 2.8 (1.8-4.9) | 7 | 3.8 (2.3-7.7) | 6.0 | delayed substrate inhibition |

*FIG. 6.*

| | mean AAG (ng/ml) | | |
|---|---|---|---|
| Genotype (n) | VV (SRD5A2) | VL | LL |
| A1A1 (CYP17) | 5.60 (66) | 4.87 (64) | 4.40 (16) |
| A1A2 | 4.94 (112) | 4.73 (85) | 4.33 (30) |
| A2A2 | 4.70 (32) | 4.05 (41) | 3.87 (12) |

*FIG. 7.*

| Allele (bp) | African-American (n = 256) | Euro-American (n = 248) | Asian (n = 120) |
|---|---|---|---|
| 271-273 | 0 | 0.008 | 0.033 |
| 275 | 0.055 | 0 | 0 |
| 281 | 0.016 | 0.020 | 0.175 |
| 283-287 | 0.004 | 0.020 | 0.008 |
| 289 | 0.336 | 0.516 | 0.367 |
| 291 | 0.254 | 0.105 | 0.150 |
| 293-295 | 0.051 | 0.012 | 0.033 |
| 302-334 | 0.066 | 0.024 | 0.125 |
| 338 | 0.039 | 0.032 | 0.008 |
| 340 | 0.137 | 0.222 | 0.075 |
| 342 | 0.023 | 0.028 | 0.017 |
| 344-372 | 0.020 | 0.016 | 0.008 |

\* Allele frequency figures were rounded as necessary and, therefore, may not add up to 1.0 (or 100% in the text)

*FIG. 8.*

ANDROGEN-METABOLIC GENE MUTATIONS AND PROSTATE CANCER RISK

CROSS-REFERENCE TO RELATED APPLICATION

This application claims the benefit of U.S. Provisional Application No. 60/072,225, filed on Jan. 23, 1998, abandoned, the entire disclosure of which is incorporated by reference in its entirety for any and all purposes.

1. FIELD OF THE INVENTION

The present invention relates to metabolic genes and their role in carcinogenesis. In particular, the invention relates to specified polymorphisms in genes encoding androgen-metabolic enzymes and their role in racial/ethnic susceptibility to prostate cancer.

2. DESCRIPTION OF RELATED ART

Metastatic prostate cancer is a leading cause of cancer-related death in men. In the United States some 334,500 men are anticipated to be diagnosed during this year and over 41,800 to die from the disease (Parker, 1997). This cancer is characterized by a marked racial/ethnic variation in risk. African-American men have the highest prostate cancer incidence rate of any racial/ethnic group, which is two-thirds higher than for White males and more than twice as high as rates for Asian-Americans. However, despite its high prevalence, very little is known regarding genetic predisposition to prostate cancer. Recent biochemical, molecular and epidemiological evidence has produced widespread interest in the role of androgens in prostate cancer pathogenesis because of their important growth regulatory effects on prostate.

Steroid hormones are ubiquitous physiologic regulators that function by modulating gene expression. Their biosynthesis involves initial conversion of cholesterol to pregnenolone which then may be metabolized by a variety of pathways to yield progestins, mineralcorticoids, glucocorticoids, androgens, and estrogens. Androgens are required for normal sexual differentiation, growth and development, and the main sexual characteristics in men. The most abundant androgen, testosterone, is produced in Leydig cells involving cytochrome P450 enzymes. Testosterone can act directly on target cells, or it can be converted into its reduced more potent form, dihydrotestosterone, by the 5α-reductase enzymes or to estradiol by the aromatase enzyme complex. Dihydrotestosterone forms a complex with the androgen receptor (AR), which translocates to the nucleus for transactivation of androgen-responsive genes and subsequent regulation of the growth of prostate cells. Dihydrotestosterone is inactivated by the 3-hydroxysteroid dehydrogenases, further modified and ultimately excreted (Coffey, 1993).

There are compelling reasons to believe that androgens play a central role in prostate carcinogenesis. The growth and maintenance of the prostate are dependent on androgens (Henderson, 1982). Prostate cancer regresses following ablative or antiandrogen therapy (Trunnel, 1950), and exogenous androgen supplementation is required in most animal prostate carcinogenesis models (Pollard, 1989; Shirai, 1995). Similarly, administration of steroid 5α-reductase inhibitors, which diminishes DHT levels, results in a substantial decrease in prostatic secretion of the normal gland and a substantial increase in cell death in normal and transformed prostatic cells (Kadohama, 1984; Lamb, 1992). Racial populations with a higher incidence of prostate cancer were shown to have a higher activity of steroid 5α-reductase (Lookingbill, 1991; Ross, 1992; Wu, 1995), and men with prostatic cancer have an increased conversion rate of testosterone to its reduced potent metabolite, dihydrotestosterone (Meikle, 1987).

Studies of the regulation of androgen biosynthesis in steroidogenic cells have focused on both transcriptional and post-translational regulation of the relevant proteins that catalyze these reactions such as the enzyme P450c17 (Picado-Leonard and Miller, 1987), the prostatic (or type II) steroid 5α-reductase, and both the 3β-hydroxysteroid dehydrogenase type II and the 17β-hydroxysteroid dehydrogenase type III. Microsomal cytochrome P450c17 is encoded by the CYP17 locus and is the key branch point in human adrenal steroidogenesis. It mediates both 17 α-hydroxylase and 17,20-lyase activities that are independently regulated (Miller, 1997). The former enzymatic activity leads to precursors of the glucocorticoid cortisol, whereas the latter activity yields precursors to the sex steroids (Brentano, 1990). Various mutations in the CYP17 gene are known that lead to deficiencies in either enzyme activity. Clinical phenotypes of these diseases include autosomal disorders producing an excess of mineralcorticoids and sexual differentiation abnormalities (Yamaguchi, 1997). Recent investigations identified a single base pair change in the 5' region of the CYP17 gene creating an SP1-type (CCACC box) promoter site in which a thymidine (T) is replaced by a cytosine (C), 34 base pairs upstream from the initiation site of translation. The normal sequence has been designated as the A1 allele and the mutated sequence as the A2 allele (Carey, 1994). It was suggested that the additional promoter site influences promoter activity, thereby increasing levels of transcription leading to elevated synthesis of androgens (Carey, 1994).

Steroid 5α-reductase acts on a variety of androgen responsive target tissues to mediate such diverse endocrine processes as male sexual differentiation in the fetus and prostatic growth in men. It also plays a role in several endocrine abnormalities. There are two isoforms of steroid 5α-reductase, type I and type II, which are encoded by the SRD5A1 and SRD5A2 gene, respectively (Wilson, 1993; Labrie, 1992; Thigpen, 1992). Type I enzyme is expressed mostly in newborn scalp and in skin and liver and is primarily responsible for virilization and male pattern baldness. Type II enzyme is primarily expressed in genital skin and the prostate and is involved in prostate development and growth (Wilson, 1993). The entire cDNA sequence of human type II SRD5A2 has been determined (Andersson, 1991), and is reproduced here:

1 gcggccaccg gcgaggaaca cggcgcgatg caggttcagt gccagca-
  gag cccagtgctg
61 gcaggcagcg ccactttggt cgcccttggg gcactggcct tgtacgtcgc
  gaagccctcc
121 ggctacggga agcacacgga gagcctgaag ccggcggcta cccgc-
  ctgcc agcccgcgcc
181 gcctggttcc tgcaggagct gccttccttc gcggtgcccg cggggatcct
  cgcccggcag
241 cccctctccc tcttcgggcc acctgggacg gtacttctgg gcctcttctg
  cgtacattac
301 ttccacagga catttgtgta ctcactgctc aatcgaggga ggccttatcc
  agctatactc
361 attctcagag gcactgcctt ctgcactgga aatggagtcc ttcaaggcta
  ctatctgatt
421 tactgtgctg aatacccctga tgggtggtac acagacatac ggtttagctt
  gggtgtcttc 481 ttatttattt tgggaatggg aataaacatt catagtgact atatattgcg ccagctcagg
541 aagcctggag aaatcagcta caggattcca caaggtggct tgtttacgta tgtttctgga
601 gccaatttcc tcggtgagat cattgaatgg atcggctatg ccctggccac ttggtccctc
661 ccagcacttg catttgcatt tttctcactt tgtttccttg ggctgcgagc ttttcaccac
721 cataggttct acctcaagat gtttgaggac taccccaaat ctcggaaagc ccttattcca
781 ttcatctttt aaaggaacca aattaaaaag gagcagagct cccacaatgc tgatgaaaac
841 tgtcaagctg ctgaaactgt aattttcatg atataatagt catatatata tatatatata
901 tatatatata tatatatatg tatatatgta atagtaggtc tcctggcgtt ctgccagctg
961 gcctggggat tctgagtggt gtctgcttag agtttactcc taccctccca gggaccccta
1021 tcctgatccc caactgaagc ttcaaaaagc cacttttcca aatggcgaca gttgcttctt
1081 agctattgct ctgagaaagt acaaacttct cctatgtctt tcaccgggca atccaagtac
1141 atgtggcttc atacccactc cctgtcaatg caggacaact ctgtaatcaa gaatttttg
1201 acttgaaggc agtacttata gaccttatta aaggtatgca ttttatacat gtaacagagt
1261 agcagaaatt taaactctga agccacaaag acccagagca aaccactcc caaatgaaaa
1321 ccccagtcat ggcttccttt ttcttggtta attaggaaag atgagaaatt attaggtaga
1381 ccttgaatac aggagccctc tcctcatagt gctgaaaaga tactgatgca ttgacctcat
1441 ttcaaatttg tgcagtgtct tagttgatga gtgcctctgt tttccagaag atttcacaat
1501 ccccggaaaa ctggtatggc tattcttgaa ggccaggttt taataaccac aaacaaaaag
1561 gcatgaacct gggtggctta tgagagagta gagaacaaca tgaccctgga tggctactaa
1621 gaggatagag aacagtttta caatagacat tgcaaactct catgttttg gaaactggtg
1681 gcaatatcca aataatgagt agtgtaaaac aaagagaatt aatgatgagg ttacatgctg
1741 cttgcctcca ccagatgtcc acaacaatat gaagtacagc agaagc-ccca agcaacttc
1801 cttttcctgga gcttcttcct tgtagttctc aggacctgtt caagaaggtg tctcctaggg
1861 gcagcctgaa tgcctccctc aaaggacctg caggcagaga ctgaaaattg cagacagagg
1921 ggcacgtctg ggcagaaaac ctgttttgtt tggctcagac atatagtttt ttttttttta
1981 caaagtttca aaaacttaaa aatcaggaga ttccttcata aaactctagc attctagttt
2041 catttaaaaa gttggaggat ctgaacatac agagcccaca tttccacacc agaactggaa
2101 ctacgtagct agtaagcatt tgagtttgca aactcttgtg aaggggtcac cccagcatga
2161 gtgctgagat atggactctc taaggaaggg gccgaacgct tgtaattgga atacatggaa
2221 atatttgtct tctcaggcct atgtttgcgg aatgcattgt caatatttag caaactgttt
2281 tgacaaatga gcaccagtgg tactaagcac agaaactcac tatataagtc acataggaaa
2341 cttgaaaggt ctgaggatga tgtagattac tgaaaaatac aaattgcaat catataaata
2401 agtgttttg ttgttcatta aataccttta aatcatg (SEQ ID NO: 1).

Germline mutations of the type II gene (SRD5A2) cause a rare human disorder, male psudohermaphroditism. Males with this disorder are phenotypically female at birth, but develop male musculature and other secondary sex characteristics at puberty (Wilson, 1993). The prostate, however, remains highly underdeveloped, and dihydrotestosterone levels are low despite a rise in testosterone in puberty, suggesting that these mutations are not implicated in prostatic diseases in adults (Thigpen, 1992). However, recent investigations have shown that the SRD5A2 gene may function as a candidate gene for predisposition to prostate cancer (Davis and Russell, 1993; Reichardt, 1995; Reichardt, 1996). Extensive genetic polymorphisms consisting of variable numbers of TA dinucleotide repeats have been identified in the 3'-untranslated region of the human SRD5A2 gene (Davis and Russell, 1993; Reichardt, 1995). Some of these polymorphisms have been shown to be unique to the highest prostate cancer risk population (African-Americans), suggesting the existence of a molecular genetic basis for the large difference in circulating levels of testosterone and the variation in racial/ethnic incidence of prostate cancer (Silver, 1994; Ross, 1995; Reichardt, 1995). Further examinations of the SRD5A2 gene revealed an additional polymorphism which was differentially distributed among racial/ethnic populations and appeared to determine in vivo steroid 5α-reductase activity (Reichardt, 1996; Makridakis, 1997).

The 3-hydroxysteroid dehydrogenases are involved in the regulation of dihydroxytestosterone levels through inactivation of this metabolite (Coffey, 1993). Two isozyme forms of 3β-hydroxysteroid dehydrogenase have been reported in humans. The type I enzyme is encoded by the HSD3B1 gene and is expressed mostly in the breast, placenta, and the skin (Labrie, 1992). The type II enzyme is encoded by the HSD3B2 gene and is primarily expressed in the adrenals, testis, and ovary (Labrie, 1992). Both genes have been cloned (Labrie, 1992) and a number of mutations in the HSD3B2 gene have been found to cause congenital adrenal hyperplasia, a rare human disorder (Rheaume, 1992). However, these and other mutations do not appear to be involved in prostatic cancer. In addition, a complex $(TG)_n$, $(TA)_n$ $(CA)_n$ dinucleotide repeat polymorphism was identified in the third intron of the HSD3B2 gene, consisting of eight alleles (Verreault, 1994). Reactions of androgens and estrogens at the C-17 position, on the other hand, are catalyzed by 17β-hydroxysteroid dehydrogenases. There have been four types (I–IV) reported and cloned which share less than 25% homology.

Current strategies to reduce the mortality rate of prostate cancer range from early detection using serologic testing for prostate-specific antigen (Catalona, 1991) to various therapeutic methods that interfere with androgen production and function (Aquilina, 1997). However, there are currently no genetic methods available for the diagnosis and prevention of prostate cancer. Thus, the identification of genetic polymorphisms controlling androgen biosynthesis and metabolism, that are responsible for predisposition of prostate cancer would provide for a better understanding of the mechanisms of cancer causation (including ethnic and individual susceptibility), and ultimately lead to ways of prostate cancer prevention. The present invention addresses these disadvantages present in the prior art.

3. SUMMARY OF THE INVENTION

The invention relates to polymorphisms in androgen-metabolic genes (SRD5A2, CYP17, HSD3B2 and HSD17B3) and to methods of using such mutations in the diagnosis and treatment of inheritable prostate cancer susceptibility.

One aspect of the invention relates to the identification of novel polymorphisms by hybridization, polymorphism and/or sequence analysis. Preferably, DNA is isolated from peripheral (blood) lymphocytes and analyzed for specific mutations by SSCP (single-strand conformation dependent DNA polymorphism) scanning and direct PCR (polymerase chain reaction) sequencing. The inheritance pattern of the specified gene polymorphisms are used to diagnose genetic susceptibility in men of various racial/ethnic populations who are genetically at increased risk for developing prostate cancer.

Other aspects of the invention include genetic probes comprising sequences complementary to the sequences containing the specified polymorphisms; cloning or expression vectors containing the nucleic acid sequences; host cells or organisms transformed with these expression vectors; methods for production and recovery of purified polypeptides from host cells; and the purified polypeptides themselves. Preferred embodiments include labeled binding agents, including antibodies, specific for the polypeptides encoded by the disclosed nucleic acids, which can be used to identify expression products of these diagnostic polymorphisms or alleles in patient derived fluid or tissue samples.

Yet other aspects of the invention relate to methods of using these nucleotide sequences or their complements, or fragments thereof, as hybridization probes, as oligomers for PCR, for chromosome and gene mapping, in the recombinant production of protein, and in generation of anti-sense DNA or RNA, their chemical analogs and the like.

For therapeutic intervention, the invention provides compositions which can functionally interfere with the transcription or translation products of the mutations and/or alleles within the specified androgen-metabolic genes associated with prostate cancer susceptibility. These include antisense nucleic acids, competitive peptides, encoded by the disclosed nucleic acids, and high affinity binding agents such as antibodies.

4. BRIEF DESCRIPTION OF DRAWINGS

FIG. 3 shows the frequency of the V89L missense substitution in 286 randomly chosen control men from four racial/ethnic groups.

Figure 1:
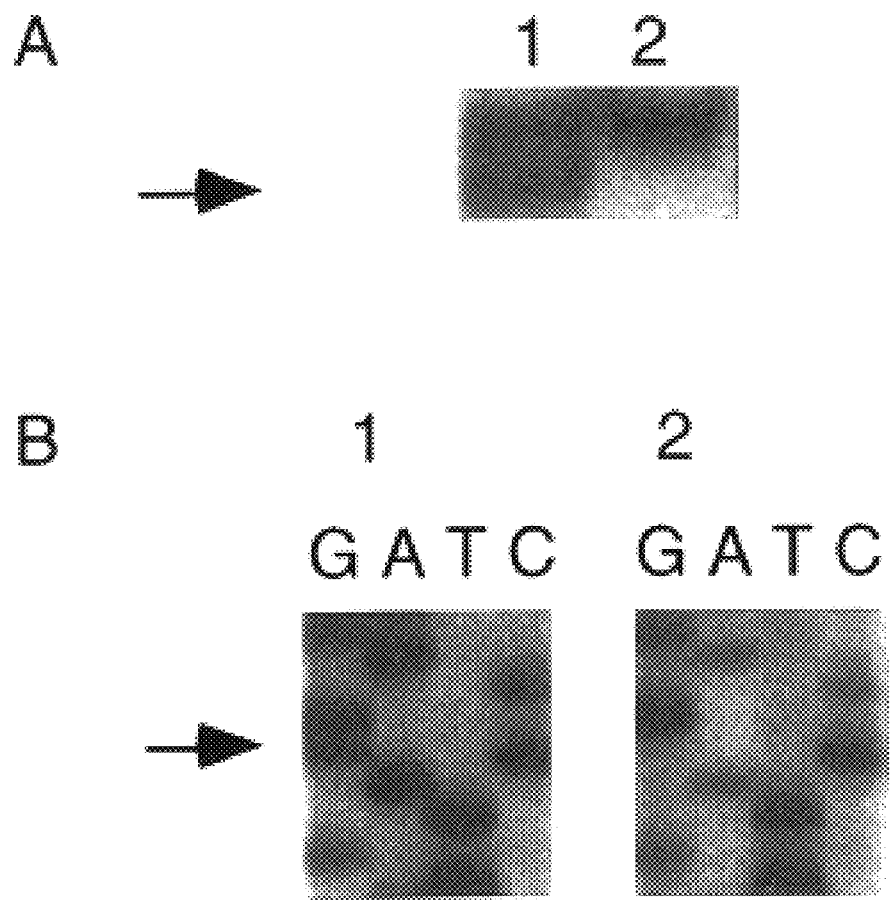
FIG. 1 illustrates the molecular identification of the V89L amino acid substitution.

FIG. 4 demonstrates the correlation between steroid 5α reductase activity and genotype at codon 89.

FIG. 5 shows the contribution of the A49T missense mutation in the SRD5A2 gene to prostate cancer risk in African-American and Latino men.

FIG. 6 describes the in vitro kinetic properties of the A49T missense mutation in the SRD5A2 gene.

FIG. 7 demonstrates androgen metabolic activity as a function of the genotype of the A1/A2 allele in the CYP17 gene and the genotype at codon 89 in the SRD5A2 gene.

FIG. 8 describes the distribution of HSD3B2 alleles in African-American, Euro-American, and Asian populations.

5. DETAILED DESCRIPTION OF THE INVENTION

5.1 Definitions

The term "allele" refers to one of two or more forms that can exist at a single gene locus (distinguished by their differing effects on the phenotype). Alleles carrying variations that predispose individuals to develop particular cancers are also called susceptibility alleles.

The expression "amplification of polynucleotides" includes methods such as PCR, ligation amplification (or ligase chain reaction, LCR) and amplification methods based on the use of Q-beta replicase. These methods are well known and widely practiced in the art. See, e.g., U.S. Pat. Nos. 4,683,195 and 4,683,202 and Innis et al., 1990 (for PCR); and Wu et al., 1989a (for LCR). Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments has been described by Scharf, 1986.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

The term "genotype" refers to the specific allelic composition of an entire cell or a certain gene, whereas the term "phenotype" refers to the detectable outward manifestations of a specific genotype.

The expression "Gleason score" is a histological grading system to indicate prognosis based on the degree of tumor differentiation or the type of glandular pattern (however, this system cannot be used to predict the progression rate of the cancer). Stage 1 disease is considered clinically inapparent prostate cancer. Stage 2 and higher is considered clinically apparent prostate cancer (stage 2+: some evidence of cancer on digital rectal exam or ultrasound).

The term "isolated" or "substantially pure" nucleic acid (e.g., an RNA, DNA or a mixed polymer) refers to a nucleic acid which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

The term "mismatches" refers to hybridized nucleic acid duplexes which are not 100% homologous. The lack of total homology may be due to deletions, insertions, inversions, substitutions or frameshift mutations.

The term "nucleotide sequence" refers to a heteropolymer of deoxyribonucleotides. Generally, nucleic acid segments provided by this invention may be assembled from fragments of the genome and short oligonucleotide linkers, or from a series of oligonucleotides, to provide a synthetic nucleic acid which is capable of being expressed in a recombinant transcriptional unit comprising regulatory elements derived from a microbial or viral operon.

The terms "oligonucleotide fragment" or "polynucleotide fragment", "portion," or "segment" refers to a stretch of polypeptide nucleotide residues which is long enough to use in PCR or various hybridization procedures to identify or amplify identical or related parts of mRNA or DNA molecules. The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "probes" includes naturally occurring or recombinant single- or double-stranded nucleic acids or chemically synthesized nucleic acids. They may be labeled by nick translation, Klenow fill-in reaction, PCR or other methods well known in the art. Probes of the present invention, their preparation and/or labeling are described in Sambrook J et al. (1989) Molecular Cloning: A Laboratory Manual, Cold Spring Harbor Laboratory, NY; or Ausubel F M et al. (1995) Current Protocols in Molecular Biology, John Wiley & Sons, New York N.Y., both incorporated herein by reference.

The term "recombinant" as it is applied to nucleic acids comprises all or part of the specified gene. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, (i) is not associated with all or a portion of a polynucleotide with which it is associated in nature; (ii) is linked to a polynucleotide other than that to which it is linked in nature; or (iii) does not occur in nature.

5.2 Nucleic Acids of the Invention

As described herein, the present invention provides a number of nucleotide sequences comprising mutations and/or alleles within the SRD5A2, CYP17, HSD3B2, or HSD17B3 genes that modulate human androgen biosynthesis and metabolism, and methods of use in the diagnosis and treatment of inheritable prostate cancer susceptibility. The disclosed mutations within the SRD5A2 gene include seven missense substitutions that resulted from the substitution of cysteine at codon 5 with arginine (C5R), proline at codon 30 with leucine (P30L), alanine at codon 49 with threonine (A49T), valine at codon 89 with leucine (V89L), threonine at codon 187 with methionine (T187M), arginine at codon 227 with glutamine (R227Q), or phenylalanine at codon 234 with leucine (F234L). The most common polymorphism is the V89L missense substitution which is due to a G to C transversion (FIG. 1). In addition, six nucleotide substitutions (C905T, C950T, T1039C, G1047T, A1395C, T2038C) are identified, which are intronic and removed from the conserved splice junctions or silent (i.e. third base pair) changes. Thus far 25 different alleles have been identified within the HSD3B2 gene (FIG. 8; Devgan, 1997). Among these, the 281 bp allele was the most prominent allele in all three populations examined, and the 275 bp allele was unique to African-American men (FIG. 8; Devgan, 1997). The sequences falling within the scope of the present invention are not limited to the specific sequences herein described, but also include nucleic acid sequences coding for the same amino acid sequences as do the disclosed sequences to accommodate for codon variability.

Also included within the scope of the specified nucleic acid sequences of the invention are antisense polynucleotides, i.e. nucleic acid sequences that hybridize under stringent conditions to a fragment of the DNA sequences carrying the specified polymorphisms, which fragment is greater than about 10 bp, preferably 20–50 bp, and even greater than 100 bp.

The present invention further provides recombinant constructs comprising a nucleic acid having the sequence of any one of the specified sequences or a fragment thereof (containing the specified polymorphism). The recombinant constructs of the present invention comprise a vector, such as a plasmid or viral vector, into which a nucleic acid having the sequence of any one of the specified sequences or a fragment thereof is inserted, in a forward or reverse orientation. The vector of choice may further comprise regulatory sequences, including for example, a promoter. Promoter regions can be selected from any desired gene using CAT (chloramphenicol transferase) vectors or other vectors with selectable markers. Selection of the appropriate vector and promoter is well within the level of ordinary skill in the art.

Generally, recombinant expression vectors will include origins of replication and selectable markers permitting transformation of the host cell. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, 1986).

5.3 Method of Detection

The present invention provides a method of identifying nucleic acid sequences containing the specified polymorphism. In detail, this method comprises (i) amplifying a DNA fragment comprising an individual's protein-coding sequence of the gene in question, (ii) comparing this DNA fragment to the sequence of the wildtype gene, and (iii) determining the presence or absence of polymorphisms in this DNA fragment. Detection of point mutations may be accomplished by molecular cloning of the specified allele and subsequent sequencing of that allele using techniques well known in the art. Alternatively, the gene sequences may be amplified directly from a genomic DNA preparation from the tumor tissue using PCR, and the sequence composition is determined from the amplified product.

The PCR reaction is well known in the art (See, e.g., Saiki, 1988; U.S. Pat. Nos. 4,683,203; and 4,683,195). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified. The primers are prepared using any suitable method, such as conventional phosphotriester or phosphodiester methods or automated embodiments thereof (Beaucage, 1981).

The polymerization agent can be any compound or system (including enzymes) which will facilitate combination of the nucleotides in the proper manner to form the primer extension products which are complementary to each nucleic acid strand. Other fundamental conditions to allow amplification include the presence of nucleoside triphosphates and suitable temperature and pH (Thigpen, 1992; Saiki, 1988).

The presence of a susceptibility allele can be established using well-known methods, some of them based on differences in hybridization of mutated against wild-type DNA segments. These methods include, but are not limited to, single-strand conformation polymorphism (SSCP) (Thigpen, 1992; Orita, 1989), denaturing gradient gel electrophoresis (DGGE) (Finke, 1996; Wartell, 1990; Sheffield, 1989), RNase protection assays (Peltonen and Pulkkinen, 1986; Osborne, 1991), allele-specific oligonucleotides (Wu, 1989), allele-specific PCR (Finke, 1996), and the use of proteins which recognize nucleotide mismatches, such as the *E. coli* mutS protein (Modrich, 1991). In addition, restriction fragment length polymorphism (RFLP) probes for the gene or surrounding marker genes can be used to score alteration of an allele or an insertion in a polymorphic fragment.

In the first three methods, the appearance of a new electrophoretic band is observed by polyacrylamide gel electrophoresis. SSCP detects the differences in speed of migration of single-stranded DNA sequences in polacrylamide gel electrophoresis under different conditions such as changes in pH, temperature, etc. A variation in the nucleotide base sequence of single-stranded DNA segments (due to mutation or polymorphism) may lead to a difference in spatial arrangement and thus in mobility. DGGE exploits differences in the stability of DNA segments in the presence or absence of a mutation. Introduction of a mutation into double-stranded sequences creates a mismatch at the mutated site that destabilizes the DNA duplex. Using a gel with an increasing gradient of formamide (denaturation gradient gel), the mutant and wild-type DNA can be differentiated by their altered migration distances. The basis for the RNase protection assay is that the RNase A enzyme cleaves mRNA that is not fully hybridized with its complementary strand, whereas completely hybridized duplex is protected from RNase A digestion. The presence of a mismatch results in incomplete hybridization and thus cleavage by RNase A at the mutation site. Formation of these smaller fragments upon cleavage can be detected by polyacrylamide gel electrophoresis. Techniques based on mismatch detection are generally being used to detect point mutations in a gene or its mRNA product. While these techniques are less sensitive than sequencing, they are simpler to perform on a large number of tumor samples. In addition to the RNase A protection assay, there are other DNA probes that can be used to detect mismatches, through enzymatic or chemical cleavage. See, e.g., Smooker and Cotton, 1993; Cotton, 1988; Shenk, 1975). Alternatively, mismatches can also be detected by shifts in the electrophoretic mobility of mismatched duplexes relative to matched duplexes (Cariello, 1988). With either riboprobes or DNA probes, the cellular mRNA or DNA which may contain a mutation can be amplified using PCR prior to hybridization. Changes in DNA of the gene itself can also be detected using Southern hybridization, especially if the changes are gross rearrangements, such as deletions and insertions.

DNA sequences of the specified gene which have been amplified by use of polymerase chain reaction may also be screened using allele-specific oligonucleotide probes. These probes are nucleic acid oligomers, each of which is complementary to a corresponding segment of the investigated gene and may or may not contain a known mutation. The assay is performed by detecting the presence or absence of a hybridization signal for the specific sequence. In case of allele-specific PCR, the PCR technique uses unique primers which selectively hybridize at their 3' ends to a particular mutated sequence. If the particular mutation is not present, no amplification product is observed.

Alteration of wild-type genes can also be detected on the basis of the alteration of a wild-type expression product of the gene. Such expression products include both the corresponding mRNA as well as the protein product. In the former case, point mutations may be detected by amplifying and sequencing the mRNA or via molecular cloning of cDNA made from the mRNA. The sequence of the cloned cDNA can be determined using DNA sequencing techniques which are well known in the art. In the latter case, the relevance of the mutated gene on the activity of the gene product was determined. In the case of the SRD5A2 gene, the activity of its gene product steroid 5α-reductase was determined by measuring serum AAG (5α androstane-3α, 17β-diol-17β-glucuronide) levels which are derived from dihydrotestosterone (which is believed to be a controlling factor in prostate carcinogenesis). Another method consists of measuring the conversion rate of testosterone into dihydrotestosterone using radioactively labeled substrate. In the latter case, the reaction products are easily separated by chromatographic means and the relative amounts of metabolites are determined by scintillation counting.

5.5 Peptides

The present invention further provides isolated polypeptides encoded by the nucleic acid fragments of the present invention or by degenerate variants of the nucleic acid fragments of the present invention. Degenerate variants represent nucleotide fragments which differ from a nucleic acid fragment of the present invention by its sequence but nevertheless encode an identical polypeptide sequence due to the degeneracy of the genetic code.

A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Fragments are useful, for example, in generating antibodies against the native polypeptide. In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography.

The polypeptides and proteins of the present invention can alternatively be purified from cells which have been altered to express the desired polypeptide or protein. One skilled in the art can readily adapt procedures for introducing and expressing either recombinant or synthetic sequences into eukaryotic or prokaryotic cells in order to generate a cell which produces one of the polypeptides or proteins of the present invention.

5.6 Antibodies

The present invention also provides polyclonal and/or monoclonal antibodies, including fragments and immunologic binding equivalents thereof, which are capable of specifically binding to the polynucleotide sequences of the specified gene (and fragments thereof) as well as the corresponding gene products (and fragments thereof). In general, techniques for preparing polyclonal and monoclonal antibodies as well as hybridomas capable of producing the desired antibody are well known in the art (Campbell, 1984; Kohler and Milstein, 1975). These include, e.g., the trioma technique and the human B-cell hybridoma technique (Kozbor, 1983; Cole, 1985).

Any animal (mouse, rabbit, etc.) that is known to produce antibodies can be immunized with the immunogenic composition. Methods for immunization are well known in the art and include subcutaneous or intraperitoneal injection of the immunogen. One skilled in the art will recognize that the amount of the protein encoded by the nucleic acids of the present invention used for immunization will vary based on the animal which is immunized, the antigenicity of the immunogen, and the site of injection. The protein which is used as an immunogen may be modified or administered in an adjuvant to increase its antigenicity. Methods of increasing antigenicity are well known in the art and include, but are not limited to, coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify hybridoma cells that produce an antibody with the desired characteristics. These include screening the hybridomas with an enzyme-linked immunosorbent assay (ELISA), western blot analysis, or radioimmunoassay (RIA) (Lutz, 1988). Hybridomas secreting the desired antibodies are cloned and the immunoglobulin class and subclass may be determined using procedures known in the art (Campbell, 1984).

Techniques described for the production of single chain antibodies (U.S. Pat. No. 4,946,778) can be adapted to produce single chain antibodies to the proteins of the present invention. For polyclonal antibodies, antibody-containing antisera is isolated from an immunized animal and is screened for the presence of antibodies with the desired specificity using one of the above described procedures.

In the present invention, the above-described antibodies are used in a labeled form to permit detection. Antibodies can be labeled, e.g., through the use of radioisotopes, affinity labels (such as biotin, avidin, etc.), enzymatic labels (such as horseradish peroxidase, alkaline phosphatase, etc.) fluorescent labels (such as fluorescein or rhodamine, etc.), paramagnetic atoms, etc. Procedures for accomplishing such labeling are well-known in the art, e.g., see Sternberger, 1970; Bayer, 1979; Engval, 1972; Goding, 1976. The labeled antibodies of the present invention can then be used for in vitro, in vivo, and in situ assays to identify the cells or tissues in which a fragment of the polypeptide of interest is expressed. Preferred immunoassays are the various types of ELISAs and RIAs known in the art (Garvey, 1977). The antibodies themselves may also be used directly in therapies or other diagnostics.

In one embodiment of the present invention the above-described antibodies are immobilized on a solid support. Examples of such solid supports include plastics such as polycarbonate, complex carbohydrates such as agarose and sepharose, acrylic resins, such as polyacrylamide and latex beads. Techniques for coupling antibodies to such solid supports are well known in the art (Weir, 1986; Jacoby, 1974). The immobilized antibodies of the present invention can be used for in vitro, in vivo, and in situ assays as well as for immuno-affinity purification of the proteins of the present invention.

5.7 Methods of Use

5.7.1 Use of Nucleic Acids as Probes

Another aspect of the subject invention is to provide for polypeptide-specific nucleic acid hybridization probes capable of detecting polynucleotide polymorphisms associated with the specified androgen-metabolic genes SRD5A2, CYP17, HSD3B2, and HSD17B3 which predispose to prostate cancer. The hybridization probes of the subject invention may be derived from the disclosed nucleotide sequences carrying the polymorphisms and form stable hybrids with the target sequences, under stringent to moderately stringent hybridization and wash conditions. Stringent conditions will be used in the case of perfect complimentarity with the target sequence, less stringent hybridization conditions will be used if mismatches are expected among the variants. Conditions will always be chosen such that nonspecific/adventitious bindings are ruled out. The probes may be of any suitable length, which span all or a portion of the specified gene region, and which allow specific hybridization.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1995. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligandbinding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like (Verma, 1988).

5.7.2 Nucleic Acid Diagnosis and Diagnostic Kits

To detect the presence of the mutations and/or alleles within the specified androgen-metabolic genes (SRD5A2, CYP17, HSD3B2, and HSD17B3) predisposing an individual to prostate cancer, a test sample is prepared and analyzed for the presence or absence of such susceptibility alleles. Thus, the present invention provides methods to identify the expression of one of the nucleic acids of the present invention, or homolog thereof, in a test sample, using a nucleic acid probe or antibodies of the present invention. In particular, such methods comprise incubating a test sample with one or more of the antibodies or one or more of nucleic acid probes of the present invention and assaying for binding of the nucleic acid probes or antibodies to components within the test sample.

Conditions for incubating a nucleic acid probe or antibody with a test sample depend on the format employed in the assay, the detection methods used, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Immunoassays: Laboratory Techniques in Biochemistry and Molecular Biology,* Elsevier Science Publishers, Amsterdam, The Netherlands (1985).

The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

5.7.3 Peptide Diagnosis and Diagnostic Kits

Similarly, the invention provides methods of using antibodies to detect differences in, or the absence of wildtype translation products of the nucleic acids of the invention. In a preferred embodiment of the invention, antibodies will immunoprecipitate the encoded proteins from solution as well as react with them on Western or immunoblots of polyacrylamide gels. In another preferred embodiment, antibodies will detect the encoded proteins in paraffin or frozen tissue sections, using immunocytochemical techniques. Techniques for raising and purifying antibodies are well known in the art, and any such techniques may be chosen to achieve the preparation of the invention. Preferred embodiments relating to methods for detecting the protein or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference.

5.7.4 Drug Screening Assay

In addition, the defective nucleic acid sequences as well as their mutant translation products, which comprise an amino acid sequence that is distinguishable from the wildtype form, can provide a target for therapeutic intervention. Binding agents that are specific for the defective androgen-metabolic genes and their gene products can be used for chemopreventive intervention. Using the isolated proteins of the present invention, the present invention further provides methods of obtaining and identifying agents which bind to one of the specified nucleic acid sequences or a protein encoded by one of the specified nucleic acid sequences.

In detail, the method comprises (i) contacting an agent with a nucleic acid sequence of the present invention or an isolated protein (or fragment thereof) encoded by one of the specified nucleic acid sequences; and (ii) determining whether the agent binds to this particular protein or nucleic acid. Furthermore, the activity of the protein is also measured to determine if the agent is capable of inhibiting the protein, and hence capable of regulating the cell cycle.

The agents screened in the above assay can be, but are not limited to, peptides, carbohydrates, vitamin derivatives, or other pharmaceutical agents. Such binding agents are obtained in various ways, including random selection and screening of existing, large libraries of natural and synthetic molecules or rational design using protein modeling techniques.

For random screening, agents such as peptides, carbohydrates, pharmaceutical agents and the like are selected at random and are assayed for their ability to bind to the protein encoded by a specified nucleic acid sequence of the present invention. Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antisense peptides, for example see Hurby, 1992, and Kaspczak, 1989, or pharmaceutical agents, or the like.

5.7.5 Gene and Peptide Therapy

According to the present invention, a method is also provided of supplying wild-type function to a cell which carries mutant alleles. The wild-type androgen-metabolic gene (SRD5A2, CYP17, HSD3B2, and/or HSD17B3) or a part thereof may be introduced into the cell in a vector such that the gene remains extrachromosomal. In such a situation, the gene will be expressed by the cell from the extrachromosomal location. More preferred is the situation where the wildtype gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate coprecipitation and viral transduction are known in the art, and the choice of method is within the competence of one skilled in the art.

As generally discussed above, the specified androgen-metabolic genes or a fragment thereof, where applicable, may be employed in gene therapy methods in order to alter the amount of the expression products of such genes in cancer cells. Such gene therapy is particularly appropriate for use in both cancerous and pre-cancerous cells, in which the level of the encoded polypeptide differs compared to normal or in those tumor cells in which the mutant gene is expressed at a "normal" level, but the gene product is affected in its performance. Gene therapy would be carried out according to generally accepted methods, for example, as described by Friedman in Therapy for Genetic Disease, 1991.

In similar fashion, peptides which have wildtype activity can be supplied to cells which carry mutant or missing alleles. The sequences of the gene products in question are well known. Protein can be produced by expression of the cDNA sequence in bacteria, for example, using known expression vectors. Alternatively, the specified polypeptide can be extracted from protein-producing mammalian cells. In addition, the techniques of synthetic chemistry can be employed to synthesize the specified protein. The protein can be introduced into cells by microinjection or by use of liposomes, for example. Alternatively, it may be taken up by cells, actively or by diffusion. Extracellular application of the gene product may be sufficient to affect tumor growth. Modified polypeptides having substantially similar function may also be used for peptide therapy.

The present invention is illustrated in the following examples.

5.8 EXAMPLES

5.8.1 Materials and Methods

Samples. The specified mutations were identified from a population-based cohort study of approximately 210,000 in size among African-American, Latino, Caucasian, and Japanese individuals aged 45–74 years in Los Angeles and Hawaii, and a similar cohort of approximately 60,000 in size among Chinese residents of Singapore. Asians in the following studies were drawn from both the Singapore and the Hawaii/Los Angeles cohorts. Participation rate for biological sample collection (blood and urine) has exceeded 70% thus far. Blood samples were processed within 4 h of collection and separated into components (lymphocytes, plasma, serum, and erythrocytes), aliquoted into plastic straws using an automated cryo-bio system, and stored in liquid nitrogen until analysis (Makridakis, 1997).

Androgen Measurement. Serum AAG levels were used as an in vivo measure for steroid 5α-reductase activity since they are derived from dihydrotestosterone, and were quantitated by using a RIA kit (available from Diagnostics Systems Laboratories, Webster, Tex.).

Molecular Analyses. Genomic DNA was extracted from white blood cells by purifying high molecular weight DNA with proteinase K digestion, followed by phenol/chloroform extraction and ethanol precipitation using standard techniques as described by Sambrook et al. in: Molecular Cloning, A Laboratory Manual, Ed.2 (1989) vol.2, p 9.16. Exon DNA to be analyzed for the presence of SSCPs in the SRD5A2 gene was PCR-amplified in the presence of a radiolabeled primer, excess of each of the four deoxynucleoside triphosphates, and thermostable DNA polymerase in buffer (Thigpen, 1992; Saiki, 1988). In the case of exon 1, the oligonucleotide primers 5'-CATCTAGAG AGCGTCCGCSAGCGGCCACCGGCGAGG-3' (SEQ ID NO: 2) and 5'-CGAAGCTTCACTGTGGAAGTAATGTA CGCAGAAGA-3' (SEQ ID NO: 3) (Thigpen, 1992) were used for amplification, and radiolabeled with $[\gamma\text{-}^{32}P]ATP$ (available from DuPont NEN, Boston, Mass.), and T4 polynucleotide kinase (available from Promega, Madison, Wis.), following standard techniques as described by Sambrook et al in: Molecular Cloning, A Laboratory Manual, Ed.2 (1989) vol.2, p. 10.13. In a preferred embodiment, the PCR products were obtained by amplification in a thermal cycler repeating 30 times the cycle consisting of denaturation at 94° C. for 1 min, annealing for 5 s at 48° C., and extension at 72° C. for 20 s. The radiolabeled and amplified exon DNA was then screened for conformation-dependent DNA polymorphisms using polyacrylamide gel electrophoresis (Thigpen, 1992; Saiki, 1988) in the presence or absence of 10% glycerol (Thigpen, 1992). A nondenatured sample of the original amplification reaction (containing molecular weight markers) was used to determine the position of migration of the double-stranded exon DNA fragment. The sequences carrying a mutation were detected by differential migration of the fragments caused by differences in single-strand intramolecular base pairing. The sequences of these mutations detected by aberrant SSCP patterns were analyzed either by a PCR-based kit (available from Life Technologies, Inc., Gaithersburg, Md., or directly with Sequenase 2.0 (available from Amersham Corp., Cleveland, Ohio) and screened for the specified mutations (Makridakis, 1997).

In the case of the CYP17 gene, a PCR fragment of the CYP17 allele was generated using the preferred primers designed from the published sequence of the 5' region of CYP17 (5'-CATTCGCACCTCTGGAGTC-3' (SEQ ID NO 4) and 5'-GGCTCTTGGGGTACTTG-3' (SEQ ID NO: 5)) (Picado-Leonard, 1987). The genomic DNA was PCR-amplified in the presence of Taq polymerase and excess of each of the four deoxynucleotide triphosphates in buffer. The amplification was for 30 cycles with denaturation at 94° C. for 1 min, annealing at 57° C. for 1 min, and extension at 72° C. for 1 min, including an initial denaturation step of 5 min at 94° C. and a final extension at 72° C. for 5 min. The PCR products were digested for 3 h at 37° C. using the restriction enzyme MspA1 and separated by agarose gel electrophoresis and staining with ethidium bromide to identify the base pair change.

In the case of the HSD3B2 gene, genomic DNA was PCR-amplified using the primer pair 5'-AATAAAGTGATTACCCTAGGTCCT-3' (SEQ ID NO:

6) and 5'-GATTGGGTCATGATACAGCCGTAG-3' (SEQ ID NO: 7) Verreault, 1994). Syntheses of the primers were performed in 30 nM scales on a Beckman Oligo1000 (Beckman Instruments, Fullerton, Calif.). In a preferred embodiment, one primer was radiolabeled by kinasing with γ[$^{32}$P]ATP (6,000 Ci/mmol; NEN, Boston, Mass.) and T4 polynucleotide kinase (Promega, Madison, Wis.). The PCR products were obtained in a TwinBlock thermal cycler (Ericomp, San Diego, Calif.) by repeating 30 times the cycle comprising (i) denaturation at 92° C. for 2 min, (ii) annealing for 1 min at 62° C., and (iii) extension at 72° C. for 2 min. PCR reactions were denatured and then fractionated on 4.5% denaturing polyacrylamide gels in parallel with DNA sequencing reactions obtained with Sequenase 2.0 (USB, Cleveland, Ohio). Gels were dried and exposed overnight to Kodak BIOMAX autoradiography films (Rochester, N.Y.) (Devgan, 1997).

Statistical Analyses. Biochemical, epidemiological, and molecular data were analyzed using standard methods as described by Colton in Statistics in Medicine (1974).

The exact method of Mehta and Patel was used to compare the overall prevalence of alleles among the three racial/ethnic groups and between each pair of groups (Mehta and Patel, 1983). All tests were statistically highly significant (two-sided, P<0.000001). Fisher's exact tests were used to test individual allele comparison (comparing each allele against all others combined) between each set of two racial/ethnic groups. Significant differences in these results were quoted as one-sided P values (EPILOG, Epicenter Software, Pasadena, Calif.).

5.8.2 Example 1

V89L Missense Substitution

Constitutional (germline) DNA from 286 randomly chosen control men from four racial/ethnic groups (African-American, Caucasian, Latino, and Asian) in the two previously described cohorts was screened for the V89L mutation located in exon 1.

The valine 89 homozygote genotype (VV) was the most common genotype found in African-Americans, Caucasians, and Latinos (FIG. 3). The highest frequency was identified among African-Americans (58.9%), and lowest in Asians (29.4%, P 0.00001). The leucine 89 homozygote genotype (LL) was most common in Asians (21.6%). Caucasians had a slightly lower frequency of the valine allele. The allele frequency for the V89L polymorphism was also statistically different between intermediate risk Caucasians and low risk Asians (FIG. 3; P=0.0002). Latino men had intermediate frequencies of the three V89L genotypes (FIG. 3).

Serum AAG levels were measured in 102 Asian individuals (FIG. 4) because they were the only racial/ethnic group with a sufficiently large number of LL homozygotes (FIG. 3). It was observed that highest AAG levels (4.72 ng/ml median among Asian controls) were found in VV homozygotes (FIG. 4) and lowest AAG levels (median of 3.40 ng/ml) were found in LL homozygotes (FIG. 4). A similar correlation between genotype and enzyme activity was made for all four racial/ethnic groups. Overall, the V89L substitution resulted in almost 30% reduced activity (FIG. 4).

5.8.3 Example 2

A49T Missense Substitution

Constitutional DNA was isolated from 120 African-American prostate cancer cases and 114 matched controls as well as 90 Latino prostate cancer cases and 107 matched controls within population-based cohort, and was screened for the A49T mutation located in exon 1. Men with prostate cancer were staged using the TNM (Tumor, Node, Metastases) system and Gleason score (Montie, 1996; Montie, 1993). TNM stage 1 with Gleason scores equal to or lower than 6 were grouped into stage 1 (clinically inapparent prostate cancer) while stage 1 with a Gleason score higher than 6 were included with TNM stages 2–8 in our stages 2 and higher (stage 2+) (clinically apparent prostate cancer).

Furthermore, the A49T mutation, which was introduced into an expressible SRD5A2 cDNA by site directed mutagenesis with custom oligonucleotides (from Life Technologies, Inc., Gaithersburg, Tex.) and the Quick-Change kit (available from Stratagene, San Diego, Calif.), was used to determine the effect on enzyme activity. 3×10$^8$ log-phase cos cells were electroporated with no DNA ("mock"), 15 μg of normal or mutant SRD5A2 constructs (Wigley, 1994) along with 5 μg of a co-transfected β-galactosidase control plasmid (pCMV β). Cell extracts were prepared 48 h post-transfection using sonication using standard techniques as described in Ausubel, et al in: Current Protocols in Molecular Biology (1995). Total protein was quantitated with a BioRad assay (BioRad Laboratories, Hercules, Calif.) and β-galactosidase activity was measured using standard techniques as described in Ausubel, et al in: Current Protocols in Molecular Biology (1995). SRD5A2 activity was determined by incubating normalized protein extracts at 37° C. and assaying aliquots for their ability to convert [$^{14}$C] testosterone to [$^{14}$C] dihydrotestosterone (available from DuPont NEN, Boston, Mass.) in the presence of the cofactor NADPH (reduced form of nicotinamide-adenine dinucleotide phosphate; available from SIGMA, St. Louis, Mo.) (Wigley, 1994). Reactions were stopped by the addition of methylene chloride, dried and redissolved steroids in ethanol were applied to K6 silica TLC (thin layer chromatography) plates (available from Whatman, Clifton, N.J.) which were developed in 12.3:1 methylenechloride/acetone (Wigley, 1994). Dried TLC plates were exposed to autoradiographic film (available from Kodak BIOMAX, Rochester, N.Y.) or directly quantitated on a Storm phosphorimager. Data were plotted and analyzed using Cricket Graph 1.3.

The A49T mutation was very rare among controls with an allele frequency of about 0.4% (1/228 chromosomes) among African-American controls and 2.3% (5/214 chromosomes) among Latino controls (FIG. 5). In African-Americans, this frequency was increased to 1.0% (1/102 chromosomes) in cases with clinically inapparent (or stage 1) disease, and 6.5% (9/138 chromosomes) with clinically apparent disease (stage 2 or higher). The population-attributable risk for stage 2+ disease was 9.3% for A49T hetero- and homozygotes in African-Americans (1-sided p=0.0049; FIG. 5). Among Latinos the allele frequency of the missense substitution was increased to 5.6% (5/90 chromosomes) in stage 1 cases and to 7.8% (7/90 chromosomes) in stage 2+ cases. The population-attributable risk for stage 2+ disease was 10.0% among Latinos (1-sided p=0.039; FIG. 5). The overall 1-sided p value for the A49T genotype for clinically apparent disease among African-American and Latino prostate cancer cases was 0.0004. The results for clinically inapparent stage 1 disease were not statistically significant. However, there was an increased frequency of the A49T genotype among stage 1 patients (FIG. 5). These findings indicate that this single SRD5A2 gene polymorphism is by far the most common genetic abnormality (in constitutional DNA) resulting in predisposition to prostate cancer. It is believed that prostate cancer will share common etiologies in various other races and ethnic groups.

Figure 2:
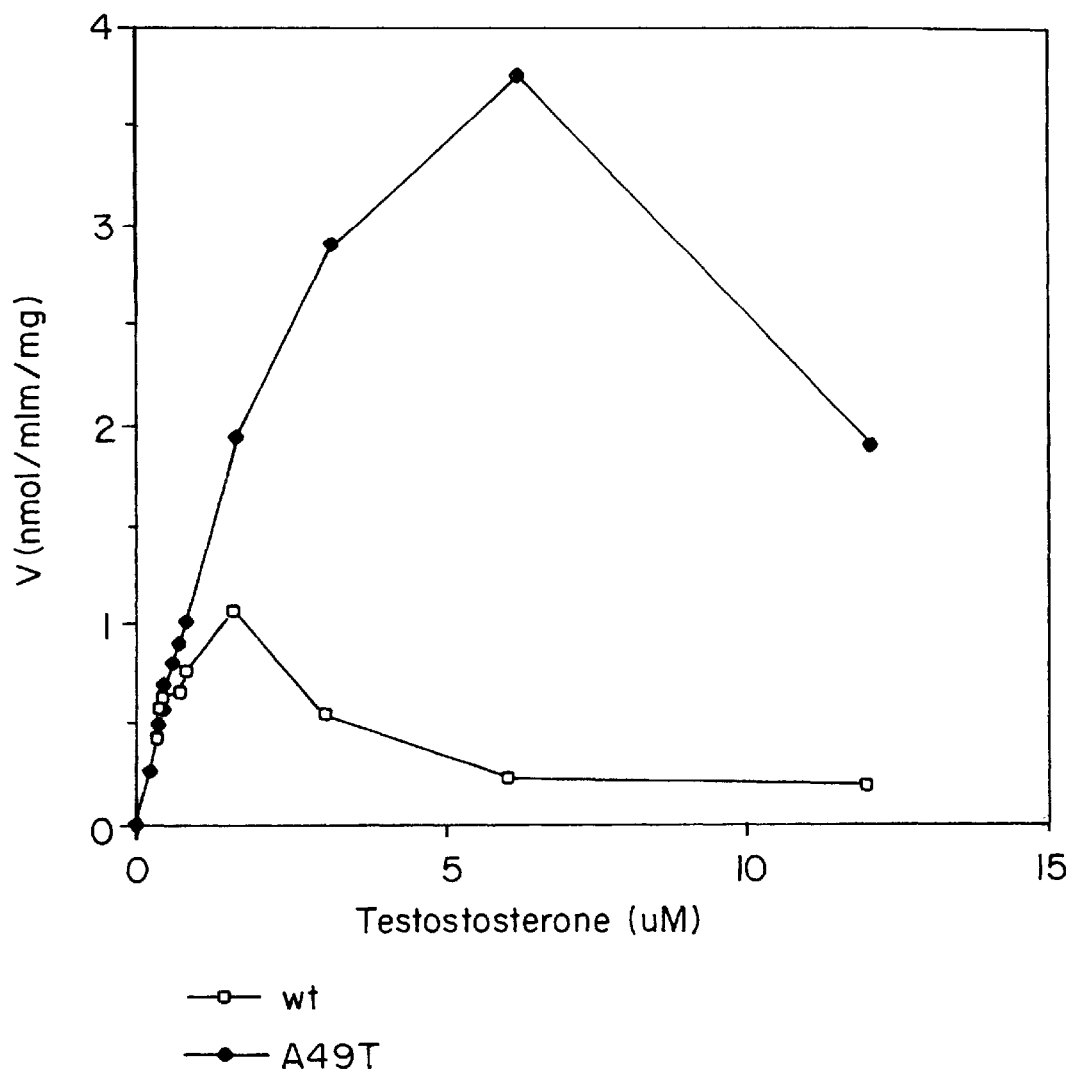
FIG. 2 illustrates the in vitro biochemical characterization of the A49T missense mutation in the SRD5A2 gene, compared to the normal (wild type) enzyme.

To determine the effect of this particular missense mutation on enzyme activity, the base pair substitution was reconstructed into the SRD5A2 cDNA. Maximum velocity ($V_{max}$) and an apparent $K_M$ for substrate (testosterone) and cofactor (NADPH) were determined. It was shown that the A49T mutation significantly increased $V_{max}$ for testosterone to dihydrotestosterone conversion (from 1.3 to 3.8 nmol× $min^{-1} \times mg^{-1}$) when compared to the normal enzyme (FIG. 2, FIG. 6) (Wigley, 1994) and affected the ability of the enzyme to bind testosterone (as illustrated by the higher $K_M$ for testosterone). Both normal and mutant enzyme have similar rates at low substrate (testosterone) levels and similar $K_M$ for the cofactor (NADPH) and pH optima (FIG. 2, FIG. 6). The A49T enzyme, however, is substrate inhibited much later (at 6 $\mu$M) than the normal enzyme (1.5 $\mu$M; FIG. 2).

These findings support the hypothesis that the association between the A49T missense mutation and prostate cancer is caused by an increase in dihydrotestosterone biosynthesis caused by elevated enzyme activity (FIG. 6; FIG. 2).

5.8.4 Example 3

V89L (SRD5A2) mutation and A1/A2 (CYP17) allele

Distribution of the A1/A2 allele in the CYP17 gene and of the V89L missense substitution in the SRD5A2 gene was examined in 458 men of African-American, Asian, Caucasian, and Latino origin. The most active human androgen-metabolic genotype, as determined by AAG levels, was the combination of A1 homozygote (A1A1) of the CYP17 gene and V homozygote (VV) of the SRD5A2 gene (FIG. 7). The least active genotype was the combination of A2 homozygote (A2A2) of the CYP17 gene and L homozygote (LL) of the SRD5A2 gene (FIG. 7). These findings suggest that both the CYP17 and the SRD5A2 gene control androgenic activity individually and that this genetic control is substantially enhanced by the bigenic combination of alleles at these two loci (FIG. 7).

5.8.5. Example 4

HSD3B2 Alleles

FIG. 8 illustrates the allele frequencies of all 25 alleles thus far identified for the HSD3B2 gene in 312 control subjects of African-American, Asian, and European heritage. The 289 bp allele was the most common allele in all three population groups examined (FIG. 8). This marker was significantly more common among Euro-Americans (allele frequency=51.6%) than among African-Americans (allele frequency=33.6%; P=0.00003) or among Asians (allele frequency=36.7%; P=0.005). The second most common allele in all populations was 291 bp in size but its frequency differed dramatically between African (allele frequency=25.4%) and Euro-Americans (allele frequency=10.5%; P=0.000009) (FIG. 8). The same allele was intermediate in frequency among Asians (allele frequency=15.0%; P=0.015 vs. African-Americans). The 275 bp allele has thus far been found only in African-American men with a frequency of 5.5% (P=0.0064 vs. Euro-Americans; P=0.0041 vs. Asians; FIG. 8). The 293–295 bp family of alleles appeared to be more common in African-Americans (allele frequency=5.1%; FIG. 8) than it was among Euro-Americans (allele frequency=1.2%; P=0.011; FIG. 8). Furthermore, alleles ranging from 302 to 334 bp in size were most common among people of Asian ancestry (allele frequency=12.5%) as was the 281 bp allele (allele frequency=17.5%). Finally, the 340 bp allele was more prominent among people from European ancestry (allele frequency=22.2%).

In summary, it is a discovery of the present invention that several missense mutations in the androgen-metabolic genes SRD5A2, CYP17, HSD3B2, and HSD17B3 are indicative of a predisposition of high risk populations to clinically apparent prostate cancer. Screening for these mutations established a differential distribution of these mutations among various racial/ethnic groups as well as altered in vivo steroid 5α-reductase activity in the case of the SRD5A2 and CYP17 gene that paralleled prostate cancer risk. It is believed that the disclosed SRD5A2 and CYP17 gene polymorphisms induce higher intraprostatic levels of dihydrotestosterone by increasing steroid 5α-reductase activity, thus amplifying the risk for developing prostate cancer. Conversely, certain hydroxysteroid dehydrogenase enzyme variants encoded by mutant HSD3B2 and HSD17B3 genes can cause slower than normal degradation of dihydrotestosterone (through decreased enzyme activity), thus also increasing the risk for developing prostate cancer.

The discovery of a causative relationship between mutation occurrence and increased prostate cancer susceptibility will allow for the development of new tools for the diagnosis, prevention and treatment of prostate cancer. Screening for these mutations (by genotyping constitutional DNA) can identify at-risk men in the general population presymptomatically for better surveillance. Furthermore, these enzyme variants provide an appropriate target for chemopreventive intervention. A binding agent of choice may interrupt the elevated dihydrotestosterone metabolism and thus reduce elevated prostate cancer risk due to these mutations.

The described invention is not limited in scope by the exemplified embodiments which are intended as an illustration for purposes of clarity and understanding, and methods which are functionally equivalent are within the scope of the invention. Various modifications of the invention may become readily apparent to those skilled in the art from the above description and these are intended to fall within the scope of the appended claims.

All publications cited within the body of the specification to illuminate the background and details of the invention are hereby incorporated by reference and for convenience grouped in the appended list of references.

6. REFERENCES

Andersson, S. et al. (1991) *Nature* 354: 159–161.
Aquilina, J. W. et al. (1997) *J. Natl. Cancer Inst.* 89: 689–696.
Ausubel, F. M. et al. (1995) *Current Protocols in Molecular Biology,* Wiley & Sons, New York, N.Y.
Bayer, E. A. et al. (1979) *Meth. Enzym.* 62: 308.
Beaucage, et al. (1981) *Tet. Lett.* 22: 1859–1862.
Brentano, S. T. et al. (1990) *Mol. Endocrin.* 4:1972–1979.
Bullock, G. R. et al., *Techniques in Immunocytochemistry,* Academic Press, Orlando, Fla. Vol. 1 (1982), Vol. 2 (1983), Vol. 3 (1985).
Campbell, A. M. (1984) *Monoclonal Antibodies Technology: Laboratory Techniques in Biochemistry and Molecular Biology,* Elsevier Science Publishers, Amsterdam, The Netherlands.
Carey, A. H. et. al. (1994) *Hum. Mol. Gen.* 3:1873–1876.
Cariello, (1988) *Human Genetics* 42: 726.
Catalona, W. J. et al. (1991) *N. Engl. J. Med.* 324: 1156–61.

Chard, T. (1986) *An Introduction to Radioimmunoassay and Related Techniques,* Elsevier Science Publishers, Amsterdam, The Netherlands.
Coffey, D. S. (1993) The molecular biology of the prostate, in Prostate Diseases, pp. 28–56. Lepor, H. and Lawson, R. K., eds., Philadelphia: W. B. Saunders.
Cole et al. (1985) in *Monoclonal Antibodies and Cancer Therapy,* Alan R. Liss, Inc., pp. 77–96.
Colton, T. (1974) *Statistics in Medicine,* Boston: Little Brown.
Cotton et al. (1988) *Proc. Natl. Acad. Sci. USA* 85: 4397.
Davis, L. et al. (1986) *Basic Methods in Molecular Biology.*
Davis, D. L. and Russell, D. W. (1993) *Hum. Mol. Genet.* 2: 820.
Devgan, S. A. et al. (1997) The Prostate 33: 9–12.
Engval, E. et al. (1972) *Immunol.* 109: 129.
Finke, R (1996) *Exp. Clin. Endocrinol. Diabetes* 104 (suppl): 92–97
Friedman (1991) *Therapy for Genetic Disease,* T. Friedman, ed., Oxford University Press, pp. 105–121.
Garvey, J. S. et al. (1977) *Methods in Immunology,* 3rd ed., W. A. Benjamin, Inc., Reading, Mass.
Goding, J. W. (1976) *J. Immunol. Meth.* 13: 215.
Henderson, B. E. et al. (1982) *Cancer Res.* 42: 3232–3239.
Hurby et al. (1992) Application of Synthetic Peptides: Antisense Peptides, In *Synthetic Peptides, A User's Guide,* W.H. Freeman, NY, pp. 289–307.
Innis et al. (1990) PCR Protocols: *A Guide to Methods and Applications,* Academic Press, San Diego.
Jacoby, W. D. et al. (1974) *Meth. Enzym.* 34 Academic Press, N.Y.
Kadohama, N. (1984) *Cancer Res.* 44: 4947–4954.
Kaspczak et al. (1989) *Biochemistry* 28: 9230–8.
Kohler, G. and Milstein, C. (1975) *Nature* 256: 495–497.
Kozbor, D. et al. (1983) *Immunology Today* 4:72.
Labrie, F. et al. (1992) *Endocrinology* 131: 1571–1573.
Labrie, F. et al (1992) *J. Steroid Biochem Mol Biol* 43: 805–826.
Lamb, J. C. (1992) *Endocrinology* 130: 685–694.
Lookingbill, D. P. (1991) *J. Clin. Endocrinol. Metab.* 72: 1242–1248.
Lutz et al.(1988) *Exp. Cell Research* 175: 109–124.
Makridakis, N. et al. (1997) *Cancer Res.* 57: 1020–1022.
Mehta, C. R and Patel, N. R. (1983) *J. Am. Stat. Assoc.* 78: 427–434.
Meikle, A. W. (1987) *Prostate* 10: 35–31.
Miller, W. L. et al. (1997) *Steroids* 62: 133–142.
Montie, J. E. et al. (1996) Staging Systems and Prognostic Factors for Prostate Cancer, in *Comprehensive Textbook of Genitourinary Oncology,* Vogelzang, N.J. et al. (eds.), Williams and Wilkins, Baltimore, Md., pp. 712–722.
Montie, J. E. (1993) Staging System for Prostate Cancer, *Seminars in Urology* 11: 10–13.
Orita, M. et al. (1989) *Proc. Nat. Acad. Sci. USA* 86: 2766–2770.
Osborne, R. J. et al. (1991) *Cancer Res.* 51: 6194–6198.
Parker, S. L. et al. (1997) *Cancer J. Clin.* 65: 5–27.
Peltonen, L. and Pulkkinen L. (1986) *Ann. Clin. Res.* 18: 224–230.
Picado-Leonard, J. and Miller, W. L. (1987) *DNA* 6: 439–448.
Pollard, M. et al. (1989) *Cancer Lett.* 45: 209–212.
Reichardt, J. K. V. et al. (1995) *Cancer Res.* 55: 3973–3975.
Reichardt, K. V. et al. ASHG 46th Annual Meeting, San Francisco. (1996) *Am. J Hum. Gen.* (suppl) 59: A187.
Rheaume, E. et al (1992) *Nature Genet* 1: 239–245.
Ross, R. K. et al. (1992) *Lancet* 339: 887.
Ross, R. K. et al. (1995) *Cancer* 75: 1778–1782.
Saiki, R. K. et al. (1988) *Science* 239: 487–491.
Sambrook, J. L. et al. (1989) *Molecular Cloning: A Laboratory Manual,* Ed.2; Cold Spring Harbor, N.Y.: Cold Spring Harbor Laboratory.
Scharf (1986) *Science* 233: 1076.
Sheffield, V. C. et al. (1989) *Proc. Nat. Acad. Sci. USA* 86: 232–236.
Shenk et al. (1975) *Proc. Natl. Acad. Sci. USA* 72: 989.
Shirai, T. et al. (1995) *Jpn. J. Cancer Res.* 86: 645–648.
Silver, R. I. et al. (1994) *J. Urol.* 152: 433–437.
Smooker, P. M. and Cotton, R. G. (1993) *Mutat. Res.* 288: 65–77.
Sternberger, L. A. et al. (1970) *J. Histochem. Cytochem.* 18: 315.
Thigpen, A. E. et al. (1992) *J. Clin. Invest.* 90: 799–809.
Tijssen, P. (1985) *Practice and Theory of Immunoassays: Laboratory Techniques in Biochemistry and Molecular Biology,* Elsevier Science Publishers, Amsterdam, The Netherlands.
Trunnel, J. B. and Duffey, B. J. (1950) *Trans. NY Acad. Sci.* 12: 238–241.
Verma et al. (1988) *Human Chromosomes: A Manual of Basic Techniques,* Pergamon Press, New York N.Y.
Verreault, H. et al (1994) *Hum. Mol. Genet.* 3: 384.
Walsh, P. S. et al. (1992) *PCR Methods Appl.* 1: 241–250.
Wartell, R. M. et al. (1990) *Nucl. Acids Res.* 18: 2699–1705.
Weir, D. M. et al. (1986) *Handbook of Experimental Immunology,* 4th Ed., Blackwell Scientific Publications, Oxford, England, Chapter 10.
Wigley, W. C. (1994) *Biochemistry* 33: 1265–1270.
Wilson, J. D. et al. (1993) *Endocr. Rev.* 14: 577–593.
Wu, A. H. (1995) *Cancer Epidemiol. Biomarkers Prev.* 4: 735–741.
Wu, D. Y. et al. (1989) *DNA* 8: 135–142.
Wu, D. Y. et al. (1989a). *Genomics* 4: 560–569.
Yamaguchi, H. et al. (1997) *J. Clin. Endocrin. Metab.* 82: 1934–1938.

What is claimed is:

1. A method for determining whether an individual is at increased risk for inheritable prostate cancer, comprising:
   (a) obtaining a sample from a patient; and
   (b) determining the presence or absence in the sample of a polymorphism in a gene, wherein said gene is SRD5A2, and wherein said polymorphism encodes an A49T missense mutation in the SRD5A2 gene product, the presence of said missense mutation being associated with increased predisposition to prostate cancer.

2. An isolated polynucleotide sequence comprising SEQ ID NO:1 having an A at nucleotide 172.

* * * * *

UNITED STATES PATENT AND TRADEMARK OFFICE
CERTIFICATE OF CORRECTION

PATENT NO. : 6,395,479 B1
DATED : May 28, 2002
INVENTOR(S) : Reichardt et al.

It is certified that error appears in the above-identified patent and that said Letters Patent is hereby corrected as shown below:

Column 1,
Line 12, please insert the following: -- This invention was made with government support under Contract No. 1 R01-CA 68581 awarded by the National Institute of Health. The government has certain rights in the invention. --

Signed and Sealed this

Twenty-ninth Day of October, 2002

Attest:

Attesting Officer

JAMES E. ROGAN
*Director of the United States Patent and Trademark Office*

SEQUENCE LISTING

<160> NUMBER OF SEQ ID NOS: 7

<210> SEQ ID NO 1
<211> LENGTH: 2437
<212> TYPE: DNA
<213> ORGANISM: Homo sapiens

<400> SEQUENCE: 1

-continued

| | | | | | |
|---|---|---|---|---|---|
| gcggccaccg | gcgaggaaca | cggcgcgatg | caggttcagt | gccagcagag | cccagtgctg | 60 |
| gcaggcagcg | ccactttggt | cgcccttggg | gcactggcct | tgtacgtcgc | gaagccctcc | 120 |
| ggctacggga | agcacacgga | gagcctgaag | ccggcggcta | cccgcctgcc | agcccgcgcc | 180 |
| gcctggttcc | tgcaggagct | gccttccttc | gcggtgcccg | cggggatcct | cgcccggcag | 240 |
| cccctctccc | tcttcgggcc | acctgggacg | gtacttctgg | gcctcttctg | cgtacattac | 300 |
| ttccacagga | catttgtgta | ctcactgctc | aatcgaggga | ggccttatcc | agctatactc | 360 |
| attctcagag | gcactgcctt | ctgcactgga | aatggagtcc | ttcaaggcta | ctatctgatt | 420 |
| tactgtgctg | aatacctga | tgggtggtac | acagacatac | ggtttagctt | gggtgtcttc | 480 |
| ttatttattt | tgggaatggg | aataaacatt | catagtgact | atatattgcg | ccagctcagg | 540 |
| aagcctggag | aaatcagcta | caggattcca | caaggtggct | tgtttacgta | tgtttctgga | 600 |
| gccaatttcc | tcggtgagat | cattgaatgg | atcggctatg | ccctggccac | ttggtccctc | 660 |
| ccagcacttg | catttgcatt | tttctcactt | tgtttccttg | ggctgcgagc | ttttcaccac | 720 |
| cataggttct | acctcaagat | gtttgaggac | taccccaaat | ctcggaaagc | ccttattcca | 780 |
| ttcatctttt | aaaggaacca | aattaaaaag | gagcagagct | cccacaatgc | tgatgaaaac | 840 |
| tgtcaagctg | ctgaaactgt | aattttcatg | atataatagt | catatatata | tatatatata | 900 |
| tatatatata | tatatatatg | tatatatgta | atagtaggtc | tcctggcgtt | ctgccagctg | 960 |
| gcctggggat | tctgagtggt | gtctgcttag | agtttactcc | tacccttcca | gggacccta | 1020 |
| tcctgatccc | caactgaagc | ttcaaaaagc | cacttttcca | aatggcgaca | gttgcttctt | 1080 |
| agctattgct | ctgagaaagt | acaaacttct | cctatgtctt | tcaccgggca | atccaagtac | 1140 |
| atgtggcttc | atacccactc | cctgtcaatg | caggacaact | ctgtaatcaa | gaattttttg | 1200 |
| acttgaaggc | agtacttata | gaccttatta | aaggtatgca | ttttatacat | gtaacagagt | 1260 |
| agcagaaatt | taaactctga | agccacaaag | acccagagca | aacccactcc | caaatgaaaa | 1320 |
| ccccagtcat | ggcttccttt | ttcttggtta | attaggaaag | atgagaaatt | attaggtaga | 1380 |
| ccttgaatac | aggagccctc | tcctcatagt | gctgaaaaga | tactgatgca | ttgacctcat | 1440 |
| ttcaaatttg | tgcagtgtct | tagttgatga | gtgcctctgt | tttccagaag | atttcacaat | 1500 |
| ccccggaaaa | ctggtatggc | tattcttgaa | ggccaggttt | taataaccac | aaacaaaaag | 1560 |
| gcatgaacct | gggtggctta | tgagagagta | gagaacaaca | tgaccctgga | tggctactaa | 1620 |
| gaggatagag | aacagtttta | caatagacat | tgcaaactct | catgtttttg | gaaactggtg | 1680 |
| gcaatatcca | aataatgagt | agtgtaaaac | aaagagaatt | aatgatgagg | ttacatgctg | 1740 |
| cttgcctcca | ccagatgtcc | acaacaatat | gaagtacagc | agaagcccca | agcaactttc | 1800 |
| cttttcctgga | gcttcttcct | tgtagttctc | aggacctgtt | caagaaggtg | tctcctaggg | 1860 |
| gcagcctgaa | tgcctccctc | aaaggacctg | caggcagaga | ctgaaaattg | cagacagagg | 1920 |
| ggcacgtctg | ggcagaaaac | ctgttttgtt | tggctcagac | atatagtttt | tttttttta | 1980 |
| caaagtttca | aaaacttaaa | aatcaggaga | ttccttcata | aaactctagc | attctagttt | 2040 |
| catttaaaaa | gttggaggat | ctgaacatac | agagcccaca | tttccacacc | agaactggaa | 2100 |
| ctacgtagct | agtaagcatt | tgagtttgca | aactcttgtg | aagggtcac | cccagcatga | 2160 |
| gtgctgagat | atggactctc | taaggaaggg | gccgaacgct | tgtaattgga | atacatggaa | 2220 |
| atatttgtct | tctcaggcct | atgtttgcgg | aatgcattgt | caatatttag | caaactgttt | 2280 |
| tgacaaatga | gcaccagtgg | tactaagcac | agaaactcac | tatataagtc | acataggaaa | 2340 |
| cttgaaaggt | ctgaggatga | tgtagattac | tgaaaaatac | aaattgcaat | catataaata | 2400 |

```
agtgttttg ttgttcatta aatacctta aatcatg                           2437

<210> SEQ ID NO 2
<211> LENGTH: 36
<212> TYPE: DNA
<213> ORGANISM: Homo sapiens

<400> SEQUENCE: 2
catctagaga gcgtccgcsa gcggccaccg gcgagg                           36

<210> SEQ ID NO 3
<211> LENGTH: 35
<212> TYPE: DNA
<213> ORGANISM: Homo sapiens

<400> SEQUENCE: 3
cgaagcttca ctgtggaagt aatgtacgca gaaga                            35

<210> SEQ ID NO 4
<211> LENGTH: 19
<212> TYPE: DNA
<213> ORGANISM: Homo sapiens

<400> SEQUENCE: 4
cattcgcacc tctggagtc                                              19

<210> SEQ ID NO 5
<211> LENGTH: 17
<212> TYPE: DNA
<213> ORGANISM: Homo sapiens

<400> SEQUENCE: 5
ggctcttggg gtacttg                                                17

<210> SEQ ID NO 6
<211> LENGTH: 24
<212> TYPE: DNA
<213> ORGANISM: Homo sapiens

<400> SEQUENCE: 6
aataaagtga ttaccctagg tcct                                        24

<210> SEQ ID NO 7
<211> LENGTH: 24
<212> TYPE: DNA
<213> ORGANISM: Homo sapiens

<400> SEQUENCE: 7
gattgggtca tgatacagcc gtag                                        24
```